United States Patent
MacDonald

(10) Patent No.: US 7,054,686 B2
(45) Date of Patent: May 30, 2006

(54) PULSEWIDTH ELECTRICAL STIMULATION

(75) Inventor: Stuart G. MacDonald, Pultneyville, NY (US)

(73) Assignee: Biophan Technologies, Inc., West Henrietta, NY (US)

( * ) Notice: Subject to any disclaimer, the term of this patent is extended or adjusted under 35 U.S.C. 154(b) by 558 days.

(21) Appl. No.: 10/243,015

(22) Filed: Sep. 13, 2002

(65) Prior Publication Data

US 2003/0055457 A1    Mar. 20, 2003

Related U.S. Application Data

(63) Continuation-in-part of application No. 09/943,216, filed on Aug. 30, 2001, now Pat. No. 6,731,979.

(51) Int. Cl.
*A61N 1/32* (2006.01)

(52) U.S. Cl. .......................................................... 607/9

(58) Field of Classification Search ................ 600/373, 600/377, 378, 393, 509, 544; 607/4, 5, 9, 607/45, 46, 117, 118, 119, 123
See application file for complete search history.

(56) References Cited

U.S. PATENT DOCUMENTS

| | | | |
|---|---|---|---|
| 3,057,356 A | 10/1962 | Greatbatch | |
| 3,478,746 A | 11/1969 | Greatbatch | |
| 3,508,167 A | 4/1970 | Russell, Jr. | |
| 3,669,095 A | 6/1972 | Kobayashi et al. | |
| 3,686,958 A | 8/1972 | Porter et al. | |
| 3,718,142 A | 2/1973 | Mulier | |
| 3,789,667 A | 2/1974 | Porter et al. | |
| 3,825,015 A | 7/1974 | Berkovits | |
| 4,012,641 A | 3/1977 | Brickerd, Jr. et al. | |
| 4,041,954 A | 8/1977 | Ohara | |
| 4,050,004 A | 9/1977 | Greatbatch | |
| 4,071,032 A | 1/1978 | Schulman | |
| 4,091,818 A | 5/1978 | Brownlee et al. | |
| 4,200,110 A | 4/1980 | Peterson et al. | |
| 4,210,029 A | 7/1980 | Porter | |
| 4,254,776 A | 3/1981 | Tanie et al. | |
| 4,325,382 A | 4/1982 | Miodownik | |
| 4,333,053 A | 6/1982 | Harrison et al. | |
| 4,341,221 A | 7/1982 | Testerman | |

(Continued)

FOREIGN PATENT DOCUMENTS

WO    WO 01/74241    10/2001

OTHER PUBLICATIONS

A. Jerwzewski et al.;, "Development of an MRI-Compatible Catheter for Pacing the Heart: Initial In Vitro and In Vivo Results." JMRI, ISHRM (US), vol. 6 (No. 6), p. 948-949, (Jun. 14, 1996).

(Continued)

*Primary Examiner*—Robert E. Pezzuto
*Assistant Examiner*—Frances P. Oropeza

(57) ABSTRACT

A process for stimulating tissue such as cardiac tissue, nerve tissue, and brain tissue. In one step of the process, there is delivered an electrical stimulating signal to the tissue that contains from about 10 to about 1,000 individual pulses. Each individual pulse has a duration of from about one microsecond to about 100 microseconds and is discontinuous, with a spacing between adjacent pulses of at least from about 1 microsecond to about 100 microseconds. The individual pulses have a voltage of from about 10 millivolts to about 100 volts.

18 Claims, 4 Drawing Sheets

U.S. PATENT DOCUMENTS

| | | |
|---|---|---|
| 4,379,262 A | 4/1983 | Young |
| 4,432,363 A | 2/1984 | Kakegawa |
| 4,450,408 A | 5/1984 | Tiemann |
| 4,476,870 A | 10/1984 | Peterson et al. |
| 4,491,768 A | 1/1985 | Slicker |
| 4,545,381 A | 10/1985 | Bournay, Jr. et al. |
| 4,611,127 A | 9/1986 | Ibrahim et al. |
| 4,677,471 A | 6/1987 | Takamura et al. |
| 4,686,964 A | 8/1987 | Yunoki et al. |
| 4,691,164 A | 9/1987 | Haragashira |
| 4,719,159 A | 1/1988 | Clark et al. |
| 4,727,874 A | 3/1988 | Bowers et al. |
| 4,763,075 A | 8/1988 | Weigert |
| 4,784,461 A | 11/1988 | Abe et al. |
| 4,798,443 A | 1/1989 | Knipe et al. |
| 4,800,883 A | 1/1989 | Winstrom |
| 4,804,244 A | 2/1989 | Hasegawa et al. |
| 4,827,906 A | 5/1989 | Robicsek et al. |
| 4,827,934 A | 5/1989 | Ekwall |
| 4,858,610 A | 8/1989 | Callaghan et al. |
| 4,879,992 A | 11/1989 | Nishigaki et al. |
| 4,880,004 A | 11/1989 | Baker, Jr. et al. |
| 4,903,701 A | 2/1990 | Moore et al. |
| 4,911,525 A | 3/1990 | Hicks et al. |
| 4,930,521 A | 6/1990 | Metzger et al. |
| 4,934,785 A | 6/1990 | Mathis et al. |
| 4,987,897 A | 1/1991 | Funke |
| 4,991,590 A | 2/1991 | Shi |
| 5,010,888 A | 4/1991 | Jadvar et al. |
| 5,055,810 A | 10/1991 | deLaChapelle et al. |
| 5,058,586 A | 10/1991 | Heinze |
| 5,061,680 A | 10/1991 | Paulson et al. |
| 5,089,697 A | 2/1992 | Prohaska |
| 5,113,859 A | 5/1992 | Funke |
| 5,131,409 A | 7/1992 | Lobarev et al. |
| 5,154,387 A | 10/1992 | Trailer |
| 5,158,932 A | 10/1992 | Hinshaw et al. |
| 5,168,871 A | 12/1992 | Grevious |
| 5,178,149 A | 1/1993 | Imburgia et al. |
| 5,214,730 A | 5/1993 | Nagasawa et al. |
| 5,217,009 A | 6/1993 | Kronberg |
| 5,217,010 A | 6/1993 | Tsitlik et al. |
| 5,226,210 A | 7/1993 | Koskenmaki et al. |
| 5,240,004 A | 8/1993 | Walinsky et al. |
| 5,243,979 A | 9/1993 | Stein et al. |
| 5,265,602 A | 11/1993 | Anderson et al. |
| 5,267,564 A | 12/1993 | Barcel et al. |
| 5,324,310 A | 6/1994 | Greeninger et al. |
| 5,330,512 A | 7/1994 | Hauck et al. |
| 5,348,010 A | 9/1994 | Schnall et al. |
| 5,354,220 A | 10/1994 | Ganguly et al. |
| 5,370,668 A | 12/1994 | Shelton |
| 5,387,229 A | 2/1995 | Poore |
| 5,387,232 A | 2/1995 | Trailer |
| 5,402,070 A | 3/1995 | Shelton et al. |
| 5,410,413 A | 4/1995 | Sela |
| 5,415,653 A | 5/1995 | Wardle et al. |
| 5,425,373 A | 6/1995 | Causey, III |
| 5,435,308 A | 7/1995 | Gallup et al. |
| 5,435,316 A | 7/1995 | Kruse |
| 5,438,987 A | 8/1995 | Thacker et al. |
| 5,445,151 A | 8/1995 | Darrow et al. |
| 5,453,838 A | 9/1995 | Danielian et al. |
| 5,456,698 A | 10/1995 | Byland et al. |
| 5,464,014 A | 11/1995 | Sugahara |
| 5,476,095 A | 12/1995 | Schnall et al. |
| 5,520,190 A | 5/1996 | Benedict et al. |
| 5,523,534 A | 6/1996 | Meister et al. |
| 5,569,158 A | 10/1996 | Suzuki et al. |
| 5,570,671 A | 11/1996 | Hickey |
| 5,574,811 A | 11/1996 | Bricheno et al. |
| 5,575,772 A | 11/1996 | Lennox |
| 5,582,170 A | 12/1996 | Soller |
| 5,590,227 A | 12/1996 | Osaka et al. |
| 5,601,611 A | 2/1997 | Fayram et al. |
| 5,603,697 A | 2/1997 | Grundy et al. |
| 5,604,433 A | 2/1997 | Theus et al. |
| 5,611,016 A | 3/1997 | Fangmann et al. |
| 5,619,605 A | 4/1997 | Ueda et al. |
| 5,626,618 A | 5/1997 | Ward et al. |
| 5,626,619 A | 5/1997 | Jacobson et al. |
| 5,631,988 A | 5/1997 | Swirhun et al. |
| 5,634,720 A | 6/1997 | Gallup et al. |
| 5,649,965 A | 7/1997 | Pons et al. |
| 5,653,735 A | 8/1997 | Chen et al. |
| 5,654,317 A | 8/1997 | Fujioka et al. |
| 5,658,966 A | 8/1997 | Tsukamoto et al. |
| 5,679,026 A | 10/1997 | Fain et al. |
| 5,683,435 A | 11/1997 | Truex et al. |
| 5,697,958 A | 12/1997 | Paul et al. |
| 5,699,801 A | 12/1997 | Atalar et al. |
| 5,709,225 A | 1/1998 | Budgifvars et al. |
| 5,716,386 A | 2/1998 | Ward et al. |
| 5,723,856 A | 3/1998 | Yao et al. |
| 5,733,247 A | 3/1998 | Fallon |
| 5,738,105 A | 4/1998 | Kroll |
| 5,749,910 A | 5/1998 | Brumwell et al. |
| 5,752,977 A | 5/1998 | Grevious et al. |
| 5,755,739 A | 5/1998 | Sun et al. |
| 5,755,742 A | 5/1998 | Schuelke et al. |
| 5,759,197 A | 6/1998 | Sawchuk et al. |
| 5,761,354 A | 6/1998 | Kuwano et al. |
| 5,766,227 A | 6/1998 | Nappholz et al. |
| 5,772,604 A | 6/1998 | Langberg et al. |
| 5,774,501 A | 6/1998 | Halpern et al. |
| 5,776,167 A | 7/1998 | Levine et al. |
| 5,776,168 A | 7/1998 | Gunderson |
| 5,782,241 A | 7/1998 | Felblinger et al. |
| 5,782,880 A | 7/1998 | Lahtinen et al. |
| 5,808,730 A | 9/1998 | Danielian et al. |
| 5,814,087 A | 9/1998 | Renirie |
| 5,814,089 A | 9/1998 | Stokes et al. |
| 5,814,090 A | 9/1998 | Latterell et al. |
| 5,814,091 A | 9/1998 | Dahlberg et al. |
| 5,817,130 A | 10/1998 | Cox et al. |
| 5,817,133 A | 10/1998 | Houben |
| 5,817,136 A | 10/1998 | Nappholz et al. |
| 5,818,990 A | 10/1998 | Steijer et al. |
| 5,827,195 A | 10/1998 | Lander |
| 5,827,997 A | 10/1998 | Chung et al. |
| 5,830,209 A | 11/1998 | Savage et al. |
| 5,836,895 A | 11/1998 | Ramsey, III |
| 5,861,012 A | 1/1999 | Stroebel |
| 5,865,839 A | 2/1999 | Doorish |
| 5,867,361 A | 2/1999 | Wolf et al. |
| 5,868,664 A | 2/1999 | Speier et al. |
| 5,869,412 A | 2/1999 | Yenni, Jr. et al. |
| 5,870,272 A | 2/1999 | Seifried et al. |
| 5,871,509 A | 2/1999 | Noren |
| 5,871,512 A | 2/1999 | Hemming et al. |
| 5,873,898 A | 2/1999 | Hemming et al. |
| 5,882,108 A | 3/1999 | Fraizer |
| 5,882,305 A | 3/1999 | Dumoulin et al. |
| 5,891,171 A | 4/1999 | Wickham |
| 5,895,980 A | 4/1999 | Thompson |
| 5,897,577 A | 4/1999 | Cinbis et al. |
| 5,899,927 A | 5/1999 | Ecker et al. |
| 5,902,326 A | 5/1999 | Lessar et al. |
| 5,916,162 A | 6/1999 | Snelton et al. |
| 5,916,237 A | 6/1999 | Schu |
| 5,917,625 A | 6/1999 | Ogusu et al. |
| 5,919,135 A | 7/1999 | Lemelson |
| 5,928,145 A | 7/1999 | Ocali et al. |
| 5,928,270 A | 7/1999 | Ramsey, III |

| | | |
|---|---|---|
| 5,928,570 A | 7/1999 | Reo |
| 5,940,554 A | 8/1999 | Chang et al. |
| 5,946,086 A | 8/1999 | Bruce |
| 5,951,596 A | 9/1999 | Bellinger |
| 5,954,660 A | 9/1999 | Legay et al. |
| 5,957,857 A | 9/1999 | Hartley |
| 5,963,034 A | 10/1999 | Mahapatra et al. |
| 5,963,690 A | 10/1999 | Cheng |
| 5,967,977 A | 10/1999 | Mullis et al. |
| 5,968,083 A | 10/1999 | Ciciarelli et al. |
| 5,973,779 A | 10/1999 | Ansari et al. |
| 5,973,906 A | 10/1999 | Stevenson et al. |
| 5,978,710 A | 11/1999 | Prutchi et al. |
| 5,982,961 A | 11/1999 | Pan et al. |
| 5,985,129 A | 11/1999 | Gough et al. |
| 5,987,995 A | 11/1999 | Sawatari et al. |
| 5,999,853 A | 12/1999 | Stoop et al. |
| 5,999,857 A | 12/1999 | Weijand et al. |
| 6,005,191 A | 12/1999 | Tzeng et al. |
| 6,011,994 A | 1/2000 | Kronberg |
| 6,013,376 A | 1/2000 | Yenni, Jr. |
| 6,016,448 A | 1/2000 | Busacker et al. |
| 6,016,477 A | 1/2000 | Ehnebuske et al. |
| 6,023,641 A | 2/2000 | Thompson |
| 6,024,738 A | 2/2000 | Daikuzono et al. |
| 6,026,316 A | 2/2000 | Kucharczyk |
| 6,029,086 A | 2/2000 | Kim et al. |
| 6,029,087 A | 2/2000 | Wohlgemuth |
| 6,031,710 A | 2/2000 | Wolf et al. |
| 6,036,639 A | 3/2000 | Allred, III et al. |
| 6,036,654 A | 3/2000 | Quinn et al. |
| 6,044,301 A | 3/2000 | Hartlaub et al. |
| 6,052,613 A | 4/2000 | Takaki |
| 6,052,614 A | 4/2000 | Morris, Sr. et al. |
| 6,052,623 A | 4/2000 | Fenner et al. |
| 6,055,455 A | 4/2000 | O'Phelan et al. |
| 6,056,415 A | 5/2000 | Alled, III et al. |
| 6,056,721 A | 5/2000 | Shulze |
| 6,064,906 A | 5/2000 | Langberg et al. |
| 6,066,096 A | 5/2000 | Smith et al. |
| 6,067,472 A | 5/2000 | Vonk et al. |
| 6,076,003 A | 6/2000 | Rogel |
| 6,080,829 A | 6/2000 | Tapsak et al. |
| 6,090,473 A | 7/2000 | Yoshikawa et al. |
| 6,090,728 A | 7/2000 | Yenni, Jr. et al. |
| 6,091,015 A | 7/2000 | delValle et al. |
| 6,091,744 A | 7/2000 | Sorin et al. |
| 6,091,987 A | 7/2000 | Thompson |
| 6,101,973 A | 8/2000 | Stewart et al. |
| 6,118,910 A | 9/2000 | Chang |
| 6,119,031 A | 9/2000 | Crowley |
| 6,129,745 A | 10/2000 | Sun et al. |
| 6,134,003 A | 10/2000 | Tearney et al. |
| 6,134,478 A | 10/2000 | Spehr |
| 6,142,678 A | 11/2000 | Cheng |
| 6,144,205 A | 11/2000 | Souza et al. |
| 6,144,866 A | 11/2000 | Miesel et al. |
| 6,144,881 A | 11/2000 | Hemming et al. |
| 6,146,415 A | 11/2000 | Fitz |
| 6,148,222 A | 11/2000 | Ramsey, III |
| 6,148,229 A | 11/2000 | Morris, Sr. et al. |
| 6,149,313 A | 11/2000 | Giebel et al. |
| 6,163,724 A | 12/2000 | Hemming et al. |
| 6,166,806 A | 12/2000 | Tjin |
| 6,169,921 B1 | 1/2001 | Ken Knight et al. |
| 6,171,240 B1 | 1/2001 | Young et al. |
| 6,173,203 B1 | 1/2001 | Barkley et al. |
| 6,179,482 B1 | 1/2001 | Takizawa et al. |
| 6,188,926 B1 | 2/2001 | Vock |
| 6,192,261 B1 | 2/2001 | Gratton et al. |
| 6,198,968 B1 | 3/2001 | Prutchi et al. |
| 6,198,972 B1 | 3/2001 | Hartlaub et al. |
| 6,208,899 B1 | 3/2001 | Kroll |

| | | | |
|---|---|---|---|
| 6,216,041 B1 | 4/2001 | Tierney et al. | |
| 6,223,083 B1 | 4/2001 | Rosar | |
| 6,226,545 B1 | 5/2001 | Gilderdale | |
| 6,230,060 B1 | 5/2001 | Mawhinney | |
| 6,236,879 B1 | 5/2001 | Konings | |
| 6,238,686 B1 | 5/2001 | Burrell et al. | |
| 6,240,317 B1 | 5/2001 | Villaseca et al. | |
| 6,245,020 B1 | 6/2001 | Moore et al. | |
| 6,246,910 B1 | 6/2001 | Bonnet et al. | |
| 6,247,474 B1 | 6/2001 | Greeninger et al. | |
| 6,254,632 B1 | 7/2001 | Wu et al. | |
| 6,256,537 B1 | 7/2001 | Stoop et al. | |
| 6,256,541 B1 | 7/2001 | Heil et al. | |
| 6,258,087 B1 | 7/2001 | Edwards et al. | |
| 6,259,843 B1 | 7/2001 | Kondo | |
| 6,259,954 B1 | 7/2001 | Conger et al. | |
| 6,263,229 B1 | 7/2001 | Atalar et al. | |
| 6,263,242 B1 | 7/2001 | Mika et al. | |
| 6,266,555 B1 | 7/2001 | Werner et al. | |
| 6,266,563 B1 | 7/2001 | Ken Knight et al. | |
| 6,266,564 B1 | 7/2001 | Hill et al. | |
| 6,266,566 B1 | 7/2001 | Nichols et al. | |
| 6,270,457 B1 | 8/2001 | Bardy | |
| 6,270,831 B1 | 8/2001 | Kumar et al. | |
| 6,272,377 B1 | 8/2001 | Sweeney et al. | |
| 6,272,380 B1 | 8/2001 | Warman et al. | |
| 6,274,265 B1 | 8/2001 | Kraska et al. | |
| 6,275,730 B1 | 8/2001 | Ken Knight et al. | |
| 6,275,732 B1 | 8/2001 | Hsu et al. | |
| 6,275,734 B1 | 8/2001 | McClure et al. | |
| 6,277,078 B1 | 8/2001 | Porat et al. | |
| 6,277,107 B1 | 8/2001 | Lurie et al. | |
| 6,278,057 B1 | 8/2001 | Avellanet | |
| 6,278,277 B1 | 8/2001 | Zeiger | |
| 6,278,894 B1 | 8/2001 | Salo et al. | |
| 6,278,897 B1 | 8/2001 | Rutten et al. | |
| 6,296,654 B1 | 10/2001 | Ward | |
| 6,317,633 B1 | 11/2001 | Jorgenson et al. | |
| 6,367,984 B1 | 4/2002 | Stephenson et al. | |
| 6,516,227 B1 * | 2/2003 | Meadows et al. | 607/46 |
| 6,647,289 B1 * | 11/2003 | Prutchi | 600/547 |
| 6,895,278 B1 * | 5/2005 | Gordon | 607/40 |
| 2002/0002390 A1 * | 1/2002 | Fischell et al. | 607/45 |
| 2005/0065562 A1 * | 3/2005 | Rezai | 607/9 |

OTHER PUBLICATIONS

W. Moshage et al., "A Non-Magnetic, MRI Compatible Pacing Center for Clinical Application in Magnetocardiography," Biomedizinixche Technik Band, Erganzungsband (Germany), p. 162-163, (Jun. 14, 1990).

C. Roos, et al., "Fiber Optic Pressure Transducer for Use Near MR Magnetic Fields," RSNA 1985; one page.

K. Wickersheim et al., "Fiberoptic Thermometry and its Applications," J. Microwave Power (1987); pp. 85-94.

Mark B. M. Hofman;"MRI-Compatible Cardiac Pacing Catheter," JMRI; May/Jun. 1997; p. 612.

A.A. Damji et al., "RF Interference Suppression in a Cardiac Synchronization System Operating in High Magnetic Field NMR Imaging System," Magnetic Resonance Imaging, vol. 6, pp. 637-640, (1988).

Frank G. Shellock et al., "Burns Associated with the use of Monitoring Equipment during MR Procedures," JMRI, Jan./Feb. 1996; pp. 271-272.

J. Nyenhuis et al., "Heating Near Implanted Medical Devices by the MRI RF-Magnetic Field," IEEE Trans. Mag.; Sep. 1999; four pages.

Frank Shellock et al., "Cardiovascular Catheters and Accessories: Ex Vivo Testing of Ferromagnetism, Heating, and Artifacts Associated with MRI," JMRL, Nov./Dec. 1998, vol. 8 #6; pp. 1338-1342.

J. Rod Gimbel et al., "Safe Performance of Magnetic Resonance," PACE; vol. 19; Jun. 1996; pp. 913-919.

National Library of Medicine; "Rapid Ventricular Pacing in a Pacemaker Patient Undergoing Magnetic Resonance Imaging," Pub Med; Pacing Clin Electrophysiol; Jun. 1998; p. 1.

National Library of Medicine;"Effects of Magnetic Resonance Imaging on Cardiac Pacemakers and Electrodes," Pub Med; Am Heart J: (1997); pp. 1-2.

M. Kusumoto et al., "Cardiac Pacing for the Clinician," Lippincott Williams & Wilkins: (2001): Chapter 1, pp. 9, 12, 13, 18, 22, 24.

Donald Fink: "Electronic Engineering," Electronic Engineers Handbook; 2nd edition, Mcgraw Hill; (1982): Section 14: pp. 29-45.

X Luo et al., "Electromagnetic Interference Shielding Using Continuous Carbon-Fiber Carbon-Matrix and Polymer-Matrix Composites," Composites Part B: Engineering: (1999): pp. 227-231.

D.D.L. Chung, "Flexible Graphite for Gasketing, Absorption, Electromagnetic Interference Shielding, Vibration Damping, Electrochemical Applications, and Stress Sensing," Journal of Materials Engineering and Performance; Apr. 2000; vol. 9 p. 161-163.

M. Konings et al., "Catheters and Guidewires in Inerventional MRI: Problems and Solutions," Medical Mundi; 45/1; Mar. (2001).

M. Konings; "Development of an MR-Safe Tracking Catheter with a Laser Driven Tip Coil," Journal of Magnetic Resonance Imaging 2001;13:131-135. c. 2001 Wiley-Liss, Inc.

EY Wong et al., "An Optical System for Wireless Detuning of Parallel Resonant Circuits" Journal of Magnetic Resonance Imaging; (2000); vol. 12, pp. 632-638.

Bernd Nowak; "Taking Advantage of Sophisticated Pacemaker Diagnostics," Excerpta Medica; (1999); pp. 172D-179D.

Jose A. Joglar et al., "Interaction of a Commercial Heart Rate Monitor With Implanted Pacemakers," Excerpta Medica; (1999); pp. 790-792.

J.A. Pomposo et al., "Polypyrrole-based Conducting Hot Melt Adhesives for EMI Shielding Applications," Elsevier; Synthetic Metals 104; (1999); pp. 107-111.

K. Grattan et al., "Fiber Optic Sensor Technology: An Overview," Elsevier; Sensors and Actuators 82; (2000);pp. 40-61.

L. Rippert et al., "Optical and Acoustic Damage Detection in Laminated CFRP Composite Materials," Elsevier; Composites Science and Technology 60; (2000); pp. 2713-2724.

C. Strandman et al., "A Production Process of Silicon Sensor Elements for a Fibre-Optic Pressure Sensor," Elsevier; Sensors and Actuators A63; (1997); pp. 69-74.

D. Howard et al., "A Single-Fringe Etalon Silicon Pressure Transducer," Elsevier: Sensors and Actuators 86; (2000); pp. 21-25.

Dan Haronian, "Displacement Sensing Using Geometrical Modulation in Reflection Mode (GM-RM) of Coupled Optical Waveguides," J. Micromech, Microeng., (UK), (1998); pp. 323-326.

H Ghafouri-Shiraz, "A Novel Distributed Feedback Laser Diode Structure foran Optical Wavelength Tunable Filter," Semicond. Sci. Technol. 12; (UK), (1997); pp. 1161-1165.

L. Kasarian, "A New Optical Fiber Multiplexer for Distortion-Free Light Transfer in Multichannel Fiber Optic Sensor Systems," Elsevier; Sensors and Actuators 84; (2000); pp. 250-258.

X. Yan et al., "Electric Field Controlled 2×2 Bypass Exchange Photorefractive Switch," IOP Publishing; (UK) (1998), pp. 383-386.

E. Piener et al., "A Micromachined Vibration Sensor Based on the Control of Power Transmitted Between Optical Fibres," Elsevier; Sensors and Actuators A65; (1998) pp. 23-29.

D. Sun et al., "High Performance Unidirectional Electrooptic Modulator Based On Polymeric Highly Multi-Mode Waveguides," Elsevier; Optics & Laser Technology 30; (1998); 481-489.

Engin Molva: "Microchip Lasers and Their Applications In Optical Microsystems," Elsevier; Optical Materials 11; (1999); pp. 289-299.

J. Linares et al., "Theory and Design of an Integrated Optical Sensor Based on Planar Waveguiding Lenses," Elsevier; Optics Communications 180; (2000); pp. 29-36.

O. Parriaux et al., "Coupling Gratings as Waveguide Functional Elements," IOP Publishing: Pure Appl. Opt. 5; (1996); pp. 453-469.

E T Enikov et al., "Three-Dimensional Microfabrication for a Multi- Degree of Freedom Capacitive Force Sensor Using Fibre-Chip Coupling" IOP Publishing; (UK); J. Micromechl. Microeng. 10;(2000) pp. 492-497.

J. Holm et al., "Through-Etched Silicon Carriers for Passive Alighnment of Optical Fibers to Surface-Active Optoelectronic Components" Elsevier;Sensors and Actuators 82; (2000) pp. 245-248.

M. Kimura et al., "Vibration Sensor Using Optical-Fiber Catilever with Bulb-Lens" Elsevier; Sensors and Actuators A66; (2000) pp. 178-183.

Y. Mao et al., "Three-Stage Wavelength Converter Based on Cross-Grain Modulation in Semiconductor Optical Amplifiers"Elsevier; Optics Communications 167; (1999) pp. 57-66.

X. Hu et al., "Dynamically Induced Irreversibility: Light Amplification and Quantum Noise Reduction in a V-Type Three-Level System" IOP Publishing; J. Opt. B: Quantum Semiclass. Opt. 2; (UK) (2000); pp. 570-575.

Y. Yim et al., "Lithium Niobate Integrated-Optic Voltage Sensorwith Variable Sensing Ranges" Elsevier; Optics Communications 152; Jul. 1, 1998; pp. 225-228.

C. Lee et al., "Electromagnetic Interference Shilding Efficiency of Polyaniline Mixtures and Multilayer Films" Elsevier; Synthetic Metals 102; (1999) pp. 1346-1349.

Marc Desmulliez, "Optoelectronics-VLSI System Integration Technological Challenges" Elsevier; Materials Science and Engineering B74;(2000) pp. 269-275.

J. Zook et al., "Fiber-optic Vibration Sensor Baed on Frequency Modulation of Light-Excited Oscillators" Elsevier; Sensors and Actuators 83; (2000); pp. 270-276.

M. Reta-Hernandez et al., "Attenuation of Low Frequency Magnetic Fields Using Active Shielding" Elsevier; Electric Power Systems Research 45; (1998); pp. 57-63.

C. Huang et al., "The EMI Shielding Effectiveness of PC/ABS/Nickel-Coated Carbon-Fibre Composites" Elsevier; European Polymer Journal 36; (2000) pp. 2727-2737.

M. Balucani et al., "Optical Link for DigitalTransmissions Using Porou Silicon Light Emitting Diode" Elsevier; Journal of Non-Crystalline Solids 266-269; (2000) pp. 1238-1240.

* cited by examiner

PULSEWIDTH ELECTRICAL STIMULATION

CROSS-REFERENCE TO RELATED PATENT APPLICATIONS

This application is a continuation-in-part of applicant's application U.S. Ser. No. 09/943,216 entitled "Pulse Width Cardiac Pacing Apparatus", filed on Aug. 30, 2001, now U.S. Pat. No. 6,731,979. The entire disclosure of U.S. Ser. No. 09/943,216 is hereby incorporated herein by reference.

FIELD OF THE INVENTION

A process for stimulating tissue in which stimulatory signals that are comprised of a multiplicity of individual pulses are delivered to a biological organism.

BACKGROUND OF THE INVENTION

Cardiac assist devices, commonly referred to as pacemakers, provide a wide range of functions but share a need to provide stimulus to the heart in order to initiate a heartbeat, to eliminate arrhythmia, or to defibrillate the heart. Traditional cardiac assist devices rely on electronic means to stimulate the heart and to monitor the presence of a normal or abnormal heartbeat. These devices typically use a battery as the source of electrical power, and much development effort has been expended in increased battery capacity and in improvements in the energy efficiency of the pacemaker systems. Further improvements in energy efficiency would benefit both the device manufacturer and the implant patient.

To the best of applicant's knowledge, none of the prior art cardiac assist devices provide means for achieving this efficiency goal. It is an object of this invention to provide an electrical stimulation system for improving the energy efficiency of a cardiac assist device by the use of pulsewidth modulation techniques that initiate cardiac excitation and contraction with signals having duty cycles far lower than one hundred percent.

Many prior art patents disclose means for sensing the response of a heart to the input from a pacemaker. Thus by way of illustration and not limitation, U.S. Pat. No. 5,957,857 discloses an improved automatic sensing system for an implantable pacemaker in which the sensing threshold is automatically set to optimally sense the P-wave or R-wave while rejecting noise. The invention of this patent is illustrative of traditional noise filtering and rejection techniques and addresses the need to sense heart function at a relatively low speed on the order of the second beat interval of the heart. The entire disclosure of this United States patent is hereby incorporated by reference into this specification.

U.S. Pat. No. 5,871,512 discloses the use of digital signal processing to detect specific signal artifacts sensed by a pacemaker, and the patent specifically relates to a movement of electrical potential in a negative direction. As with the foregoing U.S. Pat. No. 5,957,857, this measurement and analysis is done during a period in time after the entire pacing signal to the heart has been terminated. The entire disclosure of this United States patent is hereby incorporated by reference into this specification.

U.S. Pat. No. 5,330,512 deals in a similar fashion with the problem of measuring evoked potential caused by the heartbeat in the presence of much higher polarization potential in the cardiac tissues immediately disposed around the pacing electrodes. This patent further suggests the use of an additional electrode in a manner that permits the pacemaker system to make measurements of the electrical activity of myocardial tissue that are less susceptible to the effects of polarization potential. As with the foregoing patents, this patent restricts the application of its technique to a period (typically three milliseconds) following the pacing signal, which itself is typically about one millisecond in length. The entire disclosure of this U.S. patant is hereby incorporated by reference into this specification.

Thus, U.S. Pat. Nos. 5,957,857, 5,871,512, and 5,330,512 disclose improvements in sensing heart activity in an individual with an implanted pacemaker, operating in a frequency range that is consistent with the pacing signal (typically about 1 kilohertz) and with the heartbeat (typically about 1 hertz).

U.S. Pat. No. 5,782,880 discloses a low energy pacing waveform for an implantable pacemaker, and it suggests the use of a waveform different from the exponential decay waveform resulting from capacitator's discharge that is used in most pacemaker devices. This patent also discloses a pacing signal that is shaped so as to provide an adequate safety factor in reliably pacing the cardiac tissue but that reduces the energy required to do so. However, as with all other prior art devices, the device of the '880 patent utilizes a full-time signal over the approximate 1 millisecond pacing period. The entire disclosure of this patent is hereby incorporated into this specification.

Reference may also be had to texts dealing with the topic of cardiac pacing. Thus, e.g., a text entitled "Cardiac Pacing for the Clinician," edited by M. Kusumoto and N. Goldschlager, Lippincott Williams & Wilkins, Philadelphia, Pa., 2001, contains several chapter sections that deal with the physiology of cardiac pacing and sensing, and that describe the methods used by contemporary manufacturers in dealing with the issues described above. In chapter 1 on page 9 of this text, the typical safety factors employed by physicians are described; these are a 2:1 safety factor for pacing signal voltage and a 3:1 safety factor for pacing signal duration. The text further teaches that the energy dissipated in a pacing signal is directly proportional to the duration of the signal and to the square of the voltage of this signal. Thus, typical practice results in a pacing signal that is 12-fold higher than a signal that would be adequate to initiate the heartbeat. This 12-fold excess is intended to provide a very reliable pacing system, but it also may result in unnecessary acute and chronic damage to cardiac tissue and in the wastage of a majority of the energy available in the pacemaker battery.

The above text further describes, on pages 12 and 13 thereof, the nature of the evoked potential that results from the heartbeat itself, and it describes both its typical magnitude (10 to 20 millivolts) and its typical slew rate (1 to 4 volts per second).

The text further describes, on pages 18 to 24, the typical electrode structure used in pacing the heart and in sensing heart activity electrically. There is a specific discussion of the ongoing debate relating to unipolar versus bipolar pacing employing the use of one or two electrodes external to the pacemaker case, respectively.

Furthermore, and again referring to the text "Cardiac Pacing for the Clinician," (and specifically to FIG. 1.15 on page 22), it is disclosed that the stimulation threshold of the heart increases substantially after initial implantation and use. It is generally acknowledged that damage to sensitive cardiac tissues is one of the primary causes of this increase, which in requires higher pacing voltages and safety factors.

Prior art pacing systems rely on phenomena that are interpreted at the organ level, rather than the cellular or intracellular level. Thus, for instance, terms such as "capture" (describing the successful initiation of a heartbeat resulting from a pacing signal), and "refractory period" (describing the brief period following a successful pacing event during which a next heartbeat is impossible to induce with a typical pacing signal), are used to describe cause and effect at the level of the organ (in this case the heart). While there is a very well developed understanding in the literature and in the patent art of cellular-level phenomena, prior art devices have not taken advantage of this insight in the design of pacing systems. A review of the literature reveals that these cellular-level phenomena occur at speeds far faster than the timeframe of the heartbeat (1 second) or even a typical pacing signal (1 millisecond).

In an article entitled "Calcium Dynamics in the Extracellular Space of Mammalian Neural Tissue", Biophysical Journal, Volume 76, Apr. 1999, pages 1856–1867, authors David M. Egelman and P. Read Montague describe the behavior of the calcium channel during neural activity. Specifically, in FIG. 7, it is disclosed that the change in calcium concentration over time reveals a time constant on the order of 10 to 20 microseconds during the process of nerve firing. A similar analysis of FIG. 5 shows a recovery period for calcium concentration having a time constant on the order of 40 microseconds. Thus, this experimental work reveals that the total time for both the upward and downward change in calcium concentration for an individual cell involved in nerve firing to be on the order of 50 microseconds. Further, the rise time of 10 to 20 microseconds is consistent with excitation frequencies on the order of 50 to 100 kilohertz, i.e., the response to external stimulus at the cellular level occurs approximately 50 to 100 times more quickly than the typical 1 millisecond cardiac pacing signal and approximately 50,000 to 100,000 more quickly than the typical pulse rate.

More recent developments in electronic tissue stimulation systems have led to use of implantable deep brain stimulation (DBS) systems to treat essential tremor, Parkinson's disease, and epilepsy. Other advances have led to implantable vagal nerve stimulation systems to treat chronic pain. These systems share the basic attribute of stimulating brain tissue (DBS) or nerve tissue (pain therapy) with cardiac pacing systems. As a result the same benefits of this invention accrue to them as well.

It is one object of this invention to provide a cardiac assist process which takes advantage of the speed of cellular response to external stimuli, and which is substantially more energy efficient than prior art cardiac assist processes.

It is another object of this invention to provide a deep brain stimulation process which takes advantage of the speed of cellular response to external stimuli, and which is substantially more energy efficient than prior art deep brain stimulation processes.

It is a further object of this invention to provide a nerve stimulation process which takes advantage of the speed of cellular response to external stimuli, and which is substantially more energy efficient than prior art nerve stimulation processes.

SUMMARY OF THE INVENTION

In accordance one embodiment of this invention, there is provided a process for stimulating tissue selected from the group consisting of cardiac tissue, nerve tissue, brain tissue, and combinations thereof, comprising the step of delivering an electrical stimulating signal to said tissue that is comprised of from about 10 to about 1,000 individual pulses. The individual pulses each have a duration of from about microsecond to about 100 microseconds, they are discontinuous, (with a spacing between adjacent pulses of at least from about 1 microsecond to about 100 microseconds), and each of them preferably has a voltage of from about 10 millivolts to about 100 volts

BRIEF DESCRIPTION OF THE DRAWINGS

The invention will be described by reference to the specification and to the following drawings, in which like numerals refer to like elements, and in which.

DESCRIPTION OF THE PREFERRED EMBODIMENTS

The device of this invention can be used with any conventional cardiac assist device; these devices are often referred to as "pacemakers." Thus, by way of illustration, one may use such device with one or more of the pacemakers disclosed in U.S. Pat. Nos. 6,278,897, 6,278,894, 6,278,057, 6,277,107, 6,277,078 (system and method for monitoring a parameter associated with the performance of a heart), U.S. Pat No. 6,275,734 (efficient generation of sensing signals in an implantable medical device), U.S. Pat. Nos. 6,275,732, 6,272,377, 6,270,831, 6,266,564, 6,263,246 (method and apparatus for communications with an implantable device), U.S. Pat. Nos. 6,263,242, 6,259,954, 6,258,087, 6,256,541, 6,254,632 (implantable medical device having protruding surface structures for drug delivery), U.S. Pat. No. 6,247,474 (audible sound communication from an implantable medical device), U.S. Pat. No. 6,246,910 (rate response active implantable medical device), U.S. Pat. No. 6,238,686, and the like. The entire disclosure of each of these U.S. patent is hereby incorporated by reference into this specification.

Figure 1:
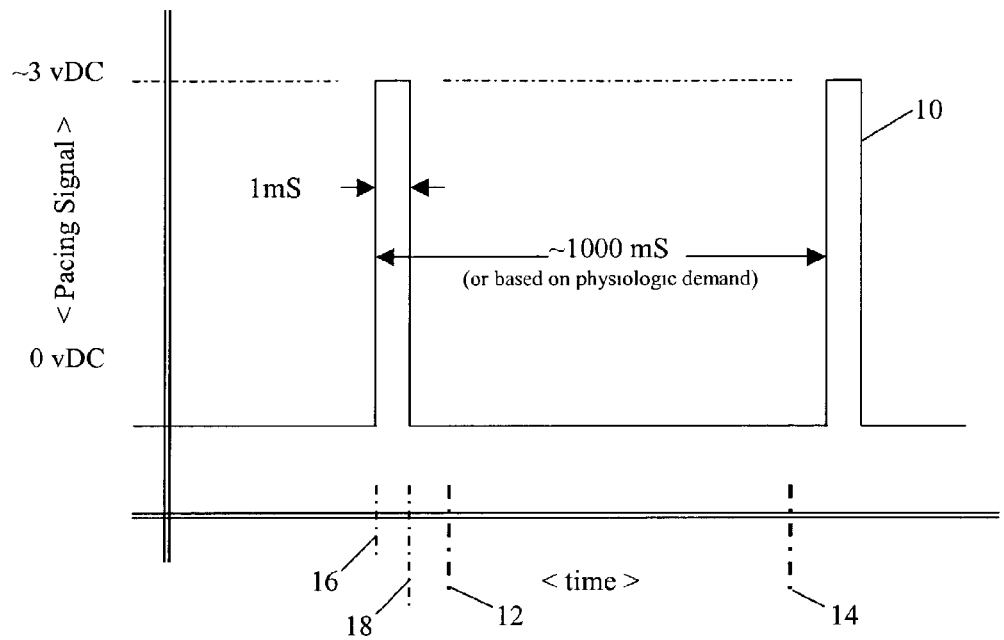
FIG. 1 is a graph depicting a typical pulse sequence used in pacing a human heart, over an interval equivalent to a nominal 1 Hz human heartbeat.

The output of a typical pacemaker is illustrated in FIG. 1, which is a graph of the electrical direct current voltage (vDC) applied to the electrode or electrodes at the distal end of a cardiac pacemaker lead, as a function of time. The indicated voltage of 3 volts d.c. (vDC) is a nominal value and is typically often selected by the physician based on the type of cardiac anomaly being corrected, the physical state of the patient's heart, and other factors. However, it should be understood that this value is intended to have a safety factor of two built into it; thus the typical voltage required to pace the heart is 1.5 volts direct current, or less.

Referring again to FIG. 1, and noting that the time axis is not to scale, the typical time between pacing events is typically about one second, or 1000 milliseconds (mS). In normal practice, using modem pacemakers, this time interval is not fixed but is variable based upon two factors. The first factor is whether or not the heart requires pacing in order to beat. The term 'demand pacemaker' applies to a device that senses heart activity electrically and does not send a pacing signal to the electrodes if the heart is beating on its own in a manner determined to be acceptable by the computer controller within the device, and based upon input programmed by the physician. Thus, during the time 12 after the refractory period associated with the previous heartbeat ends, and up to a time 14 when the next heartbeat is required, the pacemaker electrode is used to sense heart activity and to disable the next pacing signal 10 if the heartbeat is regular.

The second factor associated with demand pacing is physiologic demand; modern pacemakers are designed with additional sensing and analytical capability that permits the device to monitor physiologic demand associated with physical activity or other forms of stress that would result in an elevated heartbeat in a normal human subject. In response to this heightened physiologic demand, the pacing signal 10 would be generated at an earlier time than the delay (typically about 1000 mS) indicated in FIG. 1.

Figure 2:
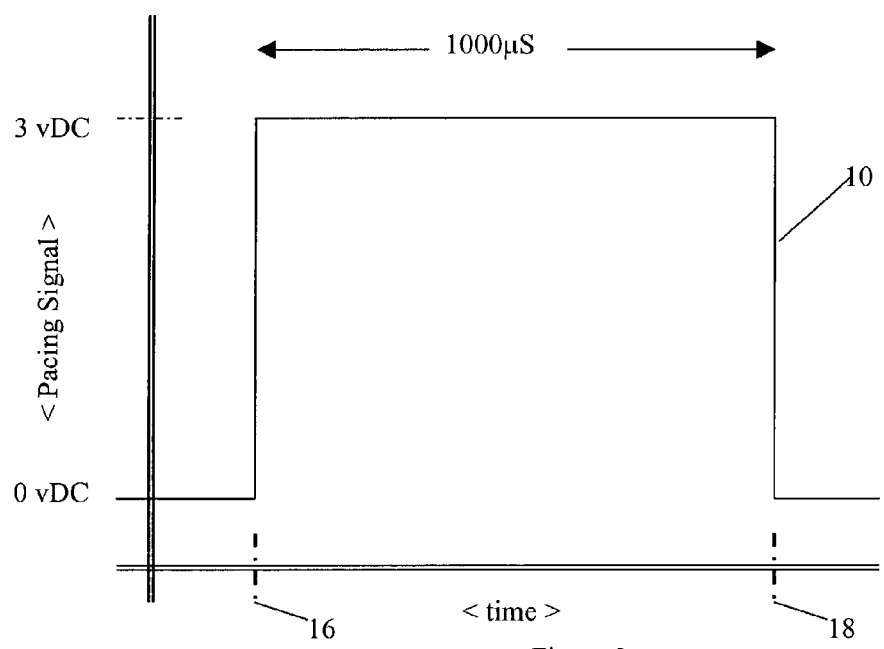
FIG. 2 is a similar graph depicting the pacing pulse as shown in FIG. 1, but with a much finer time scale.

FIG. 2 is an expanded view similar to FIG. 1, showing the pacing signal 10 over a nominal one-millisecond time interval of the actual pacing signal. The beginning of the pacing signal 16 and the end of the pacing signal 18 are shown in both FIG. 1 and FIG. 2 for reference. Note that there is no other activity in this one millisecond time interval; more particularly, there is no attempt to sense heart activity or the heart's response to the pacing signal during the time pacing time interval between times 16 and 18. This is in part due to the fact that while a relatively modest voltage (about 3 volts) is being applied to the heart cardiac tissue by the electrodes, the voltages sensed by the pacemaker in monitoring heart activity (typically in the millivolt range) would be unmeasurable using traditional techniques. In addition, the tissues surrounding the pacing electrode develop a polarization potential in response to the energy in the pacing signal; this serves to make measurements of heart activity via those same electrodes very difficult using traditional techniques. However, the interval between times 16 and 18 is very long in the context of modem computational electronic devices.

Figure 3:
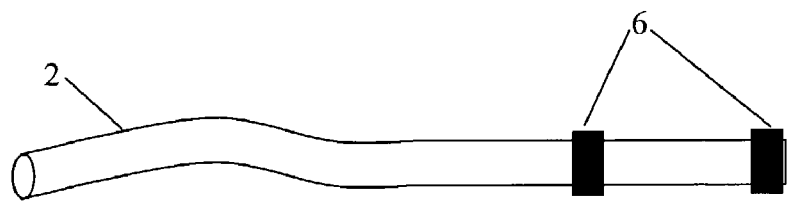
FIG. 3 is a schematic representation of a cardiac pacing lead with two electrodes.
Figure 4:
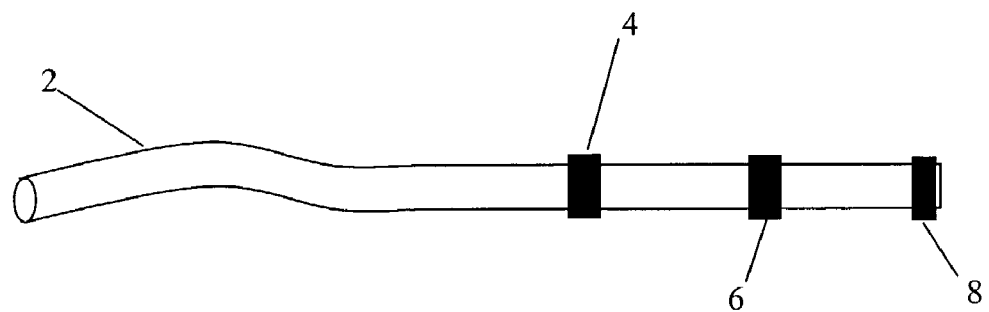
FIG. 4 is a schematic representation of a similar cardiac pacing lead with three electrodes.
Figure 5:
FIG. 5 is a schematic representation of yet another cardiac pacing lead with two pairs of electrodes.

FIGS. 3, 4, and 5 are schematic representations of a cardiac pacemaker lead 2 having various electrode configurations. In one preferred embodiment, and referring to FIG. 3, pacemaker lead 2 comprises one or more electrical conductors communicating from a connector on the body of the pacemaker device (not shown) to the electrodes 6 that are affixed by one of a number of techniques to the sensitive cardiac tissue that initiates the natural heartbeat and that is paced when necessary by the implanted pacemaker system. The configuration shown in FIG. 3 is for a bipolar pacemaker; the positive and negative terminals for electron flow through the cardiac tissue are the two electrodes 6. It should be noted that there is an alternative configuration referred to as unipolar, and it is not shown in this figure. In the case of a unipolar configuration, there is a single electrode 6 at the heart; the return path for electron flow is through the general bulk tissue back to the case of the device itself. In either unipolar or bipolar configurations, electrodes 6 are used both to pace the heart during the period between times 16 and 18 shown in FIGS. 1 and 2, but they are also used to sense heart activity electrically between times 12 and 14 shown in FIG. 1.

In the embodiment depicted in FIG. 4, sensing electrode 8 is disposed at a distance of at least about 5 millimeters from pacing electrode 4 in order to provide a degree of electrical isolation between tissues that will develop a polarization potential and tissues being sensed for heartbeat activity. Similarly, in the embodiment depicted in FIG. 5, sensing electrode pair 8 is disposed at a distance of at least about 5 millimeters from pacing electrode pair 4.

In another preferred embodiment, cardiac pacemaker lead 2 is not an electrical conductor but rather comprises one or more optical fibers that carry light energy between the pacemaker device case and the electrodes 6. This embodiment may be used in order to create pacemaker leads that are immune to the intense radio frequency and magnetic fields associated with magnetic resonance imaging (MRI), which fields can in some cases result in damage to the pacemaker and/or injury or death to the pacemaker patient who inadvertently undergoes MRI diagnosis. In this embodiment, electrodes 6 are more complex than in the former embodiment; for purposes of pacing they comprise a photodiode (not shown) used to convert light energy to electrical energy within them, and in the case of sensing cardiac activity they also comprise a miniature electrical amplifier and light emitting diode source that creates an optical signal that travels from the electrode 6 back to a pacemaker device that uses the photonic catheter of this embodiment.

In one embodiment, the pacemaker device is similar to the MRI-compatible implantable cardiac pacemaker described in a commonly-owned patent application filed on or about May 24, 2001 as docket number 1581-3 in the names of Victor Miller, Wilson Greatbatch, Patrick Connelly, and Michael Weiner, for "MRI-COMPATIBLE PACEMAKER WITH POWER CARRYING PHOTONIC CATHETHER AND ISOLATED PULSE GENERATING ELECTRONICS PROVIDING VOO FUNCTIONALITY." This commonly owned patent application was afforded serial number U.S. Ser. No. 09/865,049. The entire disclosure of this commonly owned patent application is hereby incorporated by reference into this patent application.

The U.S. Ser. No. 09/865,049 case describes a "V00 pacemaker," which, as is known to those skilled in the art, is asynchronous, having no feedback signal from the heart. By comparison, the pacemaker of the instant invention uses components and circuitry similar in nature to those described in such application but for purposes of transducing pacing signals to the heart and transducing sensing signals from the heart.

Thus, by way of illustration, one may utilize the photonic catheter components illustrated in FIGS. 2 and 2A of the U.S. Ser. No. 09/865,049 case (see, e.g., the description of these components at pages 11, 12, and 13 of such case).

Thus, by way of further illustration, one may utilize the pulsed signal generator circuits illustrated in FIGS. 4 and 5 of the U.S. Ser. No. 09/865,049 case (see, e.g., the description of these circuits at pages 13, 14, and 15 of such case).

Thus, e.g., the device disclosed in U.S. Pat. No. 5,454,837 might advantageously utilize the instant invention. Such patent claims a medical system for implantation in a body containing body tissue comprising: an implantable housing containing therapy-generating means for generating electrical signals; an implantable optical conductor having a first end and a second end; means for attaching said first end of said optical conductor to said therapy-generating means; implantable electrical means for in vivo electrically interacting with said body tissue; means for attaching said electrical means to said second end of said optical conductor; first converter means disposed at said first end of said optical conductor for converting said electrical signals into corresponding optical signals, said optical signals being transmitted by said optical conductor to said second end of said optical conductor; and second converter means disposed at said second end of said optical conductor for converting said optical signals into corresponding electrical signals supplied to said electrical means. The entire disclosure of this United States patent is hereby incorporated by reference into this specification.

In another embodiment, and referring to FIG. 4, the pacemaker lead 2 connects the pacemaker device case (not shown) to a set of electrodes 4, 6, and 8 at its distal end and affixed to cardiac tissue as in the previous embodiment. Electrode 6, as in the previous embodiment, is capable of either pacing the heart or sensing heart activity electrically. Electrode 4 is used only to pace the heart, and is identical in its function to that part of the function of the dual-purpose electrode 6. In like manner electrode 8 is used only for sensing heart activity electrically, in a fashion identical to that part of the function of the dual-purpose electrode 6. The reason for the configuration shown in FIG. 4 is that the cardiac tissue immediately involved in the pacing event, and which develops a polarization potential as a result of the pacing signal, is somewhat removed physically from the cardiac tissue immediately around the sensing electrode 8, thus providing some degree of isolation from polarization potential in the area where cardiac sensing is being done, but still providing ample opportunity for sensing any cardiac activity. Thus this embodiment provides the opportunity for sensing measurements to be made during dwell periods in the overall pacing signal wherein no voltage is being applied to the cardiac tissue.

In a further embodiment, and still referring to FIG. 4, pacemaker lead 2 does not contain electrical conductors but rather comprises one or more optical fibers, as described elsewhere in this specification. Likewise, electrodes 4 and 6 have the capability to convert optical energy to electrical energy in order to pace the heart, and electrodes 6 and 8 comprise electrical amplifier and electricity-to-light conversion, as is also described in the previous embodiment.

In yet another preferred embodiment, shown in FIG. 5, pacemaker lead 2 connects the pacemaker device case (not shown) to a set of electrodes 4 and 8 at its distal end and is affixed to cardiac tissue as in the previous embodiments. In this embodiment, additional separation between the volume of cardiac tissue being paced (between electrodes 4) and the volume of cardiac tissue being sensed (between electrodes 8) is created in order to provide further improvements in electrical isolation between those areas, thereby providing further improvement in the ability to make sensing measurements during cardiac pacing.

In yet another embodiment, and still referring to FIG. 5, pacemaker lead 2 does not contain electrical conductors but rather contains one or more optical fibers, as elsewhere in this specification. Likewise, electrodes 4 have the capability to convert optical energy to electrical energy in order to pace the heart, and electrodes 8 comprise electrical amplifier and electricity-to-light conversion as also described in previous embodiments.

Figure 6:
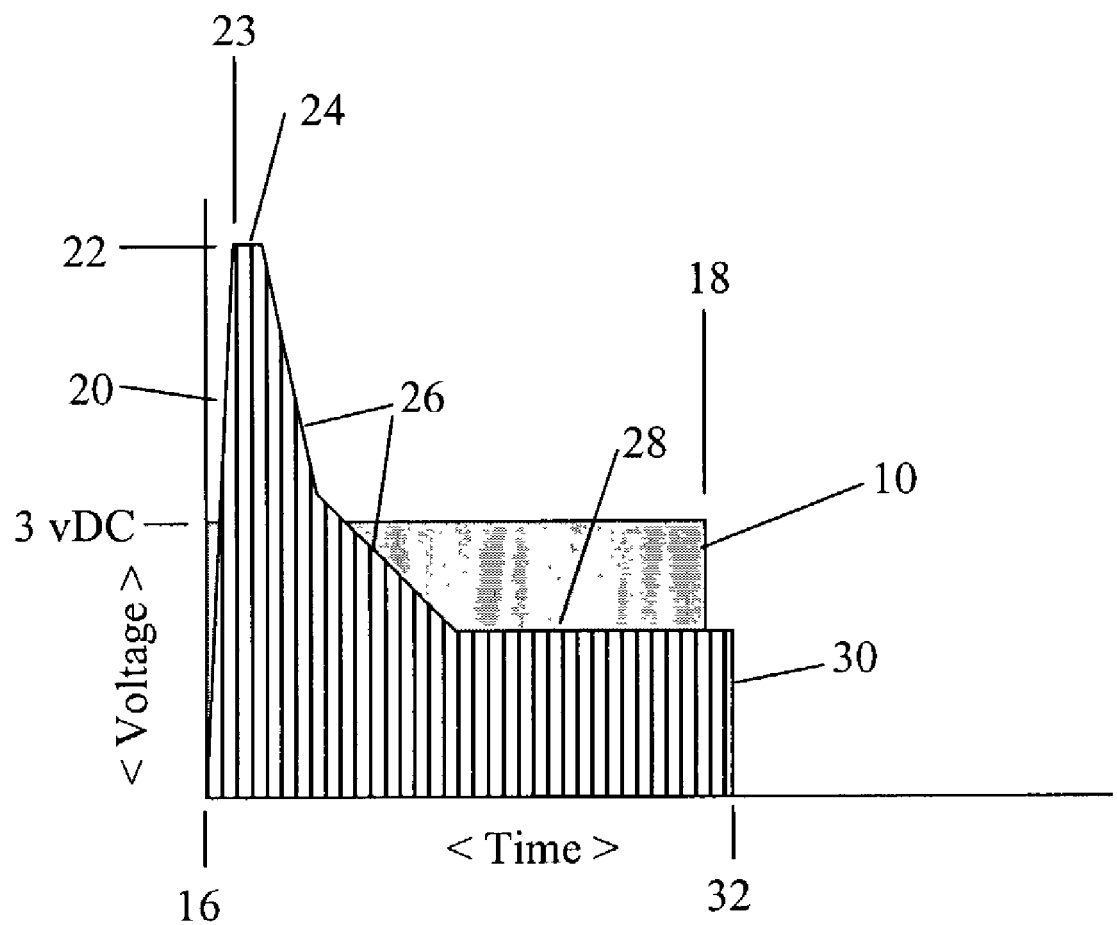
FIG. 6 is a graph depicting the use of pulsewidth pacing signals to pace the heart with lower overall energy expenditure.

In one preferred embodiment of this invention, a technique of pulsewidth modulation is used to pace the heart. Referring to FIG. 6, a traditional cardiac pacing pulse 10 having a nominal voltage of about 3 vDC begins at time 16 and ends at time 18, as also shown in FIGS. 1 and 2 and discussed above.

Referring again to FIG. 6, a more complex set of high frequency pulses is shown and will be described by reference to its several parts. The initial front-end rise 20 reaches peak voltage 22 at time 23, which is determined by the input voltage and the overall impedance of the aggregate system that comprises the pulse generator, the leads, the electrodes, the electrode-tissue interface, and the bulk tissue between the anodic and cathodic tissue interfaces. Peak voltage 22 may be of about the same level as in a traditional pacing pulse, that is to say about 2 to 4 vDC, or it may be substantially higher. Additionally, the length of time the peak voltage is maintained may range from zero to as much as one hundred microseconds or more. During the period after which the initial peak voltage level is reached, the pacing system of this invention reverts to a pulsewidth mode of operation. Those skilled in the art will recognize pulsewidth modulation as a technique broadly applied across electrical and electronic control systems to deliver power in a manner that makes optimal and efficient use of a fixed supply voltage, while delivering power to a device or system that requires variable voltage to carry out its intended function. This is done by switching the supply voltage on and off at high frequency with a duty cycle, which is defined as the portion of time the supply voltage is turned on, that results in effectively delivering lower and infinitely variable voltage to the device or system being powered. By way of example, U.S. Pat. No. 4,455,599, "Pulse width modulation inverter," discloses a method of halting a PWM inverter without causing a short-circuit mode in the three-phase bridge connection constituting the inverter. U.S. Pat. No. 4,491,768 discloses an inverter that is connected between a source of DC power and a three-phase AC induction motor, and a microprocessor-based circuit controls the inverter using pulse width modulation techniques. U.S. Pat. No. 4,727,874 discloses a pulse width modulation technique that regulates the output power of each cycle of a radio frequency surgical signal of an electro-surgical generator, the delivered power of the surgical signal being determined by multiplying the sensed current and the sensed voltage of the surgical signal. The entire disclosure of each of these United States patents is hereby incorporated by reference into this specification.

By way of further illustration, and referring to pages 14–29 et seq. of Donald G. Fink's "Electronics Engineers' Handbook," Second Edition (McGraw Hill Book Company, New York, N.Y., 1982), it will be seen that a high frequency signal made up of individual pulses, all of the same voltage, but having duty cycles less than 1.0, will produce an effective applied voltage equivalent to the duty cycle multiplied by the applied pulse voltage.

Referring again to FIG. 6, peak voltage 22 is maintained throughout initiation phase 24, and then is reduced during transient phase 26 to a lower level that is held during maintenance phase 28, until the signal ends at cutoff 30 at time 32. It should be understood that cutoff 30 may occur at a time 32 that is later than time 18 for a traditional pacing pulse, as shown, or it may occur at a time 32 that is sooner than time 18.

The graph of FIG. 6 indicates actual supply voltages that change during transient phase 26, and FIG. 6 is intended to be illustrative only in that a variety of waveforms may be used in order to optimize the reliability of pacing for an individual pacemaker patient. Thus FIG. 6 could depict more complex waveforms having a multiplicity of curvilinear shapes in order to address the specific requirements of cardiac pacing.

Referring again to FIG. 6, and of key importance in the practical design of a device of this invention, is that fact that the supply voltage used during front-end rise 20, initiation phase 24, transient phase 26, and maintenance phase 28 may be the same. The effective energy delivered to the sensitized cardiac cells can be derived from a single supply voltage by use of pulsewidth modulation techniques previously discussed.

The supply voltage chosen for the pulsewidth modulation control technique of this invention should be at least as high as the peak voltage 22 in FIG. 6, and may advantageously be substantially higher that peak voltage 22 in order to minimize rise time, that is to minimize the time between time 16 and time 23 as shown in FIG. 6. The use of a single supply voltage and pulsewidth modulation techniques provides for optimal efficiency since modem electronic controllers switch at frequencies in excess of megahertz, and with near one hundred percent efficiency.

Thus, by way of illustration and not limitation, the pacemaker system using the instant invention may comprise means for controlling arrhythmia and/or providing defibrillation. Reference may be had, e.g., to U.S. Pat. Nos. 6,278, 897, 6,275,730 (method and apparatus for treating cardiac arrhythmia), U.S. Pat. No. 6,274,265 (implantable medical device), U.S. Pat. No. 6,272,380 apparatus for treating atrial tachyarrhythmias), U.S. Pat. Nos. 6,270,457, 6,266,566, 6,266,564, 6,266,563 (method and apparatus for treating cardiac arrhythmia), U.S. Pat. Nos. 6,266,555, 6,256,537 (pacemaker system with inhibition of AV node for rate regulation during atrial fibrillation), and the like. The entire disclosure of each of these United States patents is hereby incorporated by reference into this specification.

Referring again to the text "Cardiac Pacing for the Clinician," and specifically to FIG. 1.15 on page 22, it may be seen that the stimulation threshold of the heart increases substantially after initial implantation and use. Damage to sensitive cardiac tissues is one of the primary causes of this increase, which in requires higher pacing voltages and safety factors. By practicing this invention, thus substantially reducing the energy applied to sensitive cardiac tissues, increases in stimulation threshold may be substantially reduced.

Referring yet again to the text "Cardiac Pacing for the Clinician," and specifically to the discussion of the polarization effect at the electrode on pages 5 and 6, it may further be seen that by using substantially lower power level and pulse duration to pace the heart, the effects of polarization potential will be reduced; this reduces the effective impedance of cardiac tissue at the tissue/electrode interface, and reduces the background potential that interferes with sensitive measurements of cardiac tissue activity.

Figure 7:
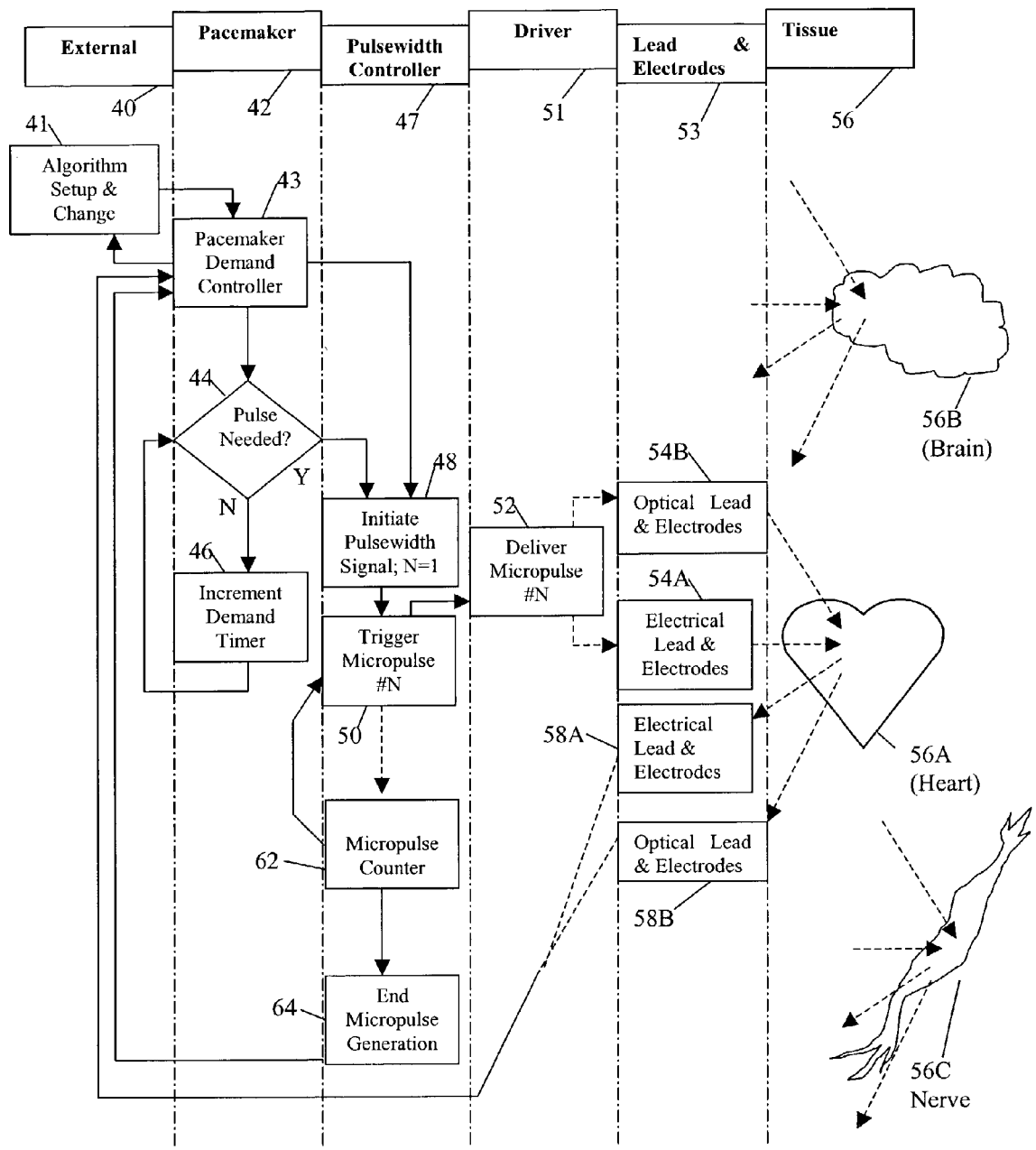
FIG. 7 is a flow chart illustrating one preferred process of the invention.

FIG. 7 is a flowchart depicting the process used to pace a heart with the aforementioned pulsewidth technique, to monitor the response of the cardiac tissue after the pacing pulse is delivered to determine capture and a successful heartbeat. This specification describes the process that would be used in a pacemaker typically referred to as a demand pacemaker. Further detail regarding this type of pacemaker may be found in Chapter 3 of the previously cited text "Cardiac Pacing for the Clinician." However, the invention described herein, and in particular the process depicted in the flowchart of FIG. 7, may be applied to all forms of pacemakers in current use, and by extension may be applied to any form of implantable stimulation device.

Referring to FIG. 7, external programmer 40 communicates with the pacemaker control computer 42 via any of a number of techniques, including but not limited to radio frequency, magnetic, acoustic, and near infrared light technique. One of the functions of the external programmer 40 is the initial setup conditions for the control algorithm 41; these are chosen by the physician, for the specific patient, based upon said patient's physical condition, the specific cardiac abnormality being treated, and other factors such as age, gender, and the like. Another function of programmer 40 is to adjust control algorithm 41 at later times depending upon changes in the patient's condition, or based upon feedback received from the pacemaker; in either case the physician may direct these changes or they may be designed into the software resident in external programmer 40.

Pacemaker controller 42 has as one of its functions the control of the pacing of the heart based upon physiologic demand. For purposes of this specification, the simplifying assumption will be made that pacemaker controller 42 monitors the patient's physiologic state and directs demand controller 43 to pace the heart at a rate determined by an algorithm residing in pacemaker controller 42. Thus the function of demand controller 43 is simply to monitor the heart during the period between times 12 and 14 from FIG. 1; and, if the heart does not initiate a heart beat within that interval, the pacemaker then initiates a pacing signal, typically about 3 volts and having a duration of about 1 millisecond, via a standard lead and electrodes. Demand pacemakers and other cardiac assist devices receive feedback information from the heart in the interval between beats, so the logical function shown in FIG. 7 as a pulse/no pulse decision 44 and a step of resetting the timer within the demand controller 46 comprises substantially all of the timing logic employed by said devices.

Thus, by way of illustration and not limitation, the pacemaker controller 42 may comprise means for controlling arrhythmia and/or providing defibrillation. Reference may be had, e.g., to U.S. Pat. Nos. 6,278,897, 6,275,730 (method and apparatus for treating cardiac arrhythmia), U.S. Pat. No. 6,274,265 (implantable medical device), U.S. Pat. No. 6,272,380 apparatus for treating atrial tachy arrhythmias), U.S. Pat. Nos. 6,270,457, 6,266,566, 6,266,564, 6,266,563 (method and apparatus for treating cardiac arrhythmia), U.S. Pat. Nos. 6,266,555, 6,256,537 (pacemaker system with inhibition of AV node for rate regulation during atrial fibrillation), and the like. The entire disclosure of each of these United States patents is hereby incorporated by reference into this specification.

Referring again to FIG. 7, and in the embodiment depicted therein, it may be seen that this invention preferably employs another layer of timing logic contained in pulsewidth controller 47. In this embodiment, pacemaker demand controller 43 provides programmatic input to said pulsewidth controller, said input including recent history of the patient's physiologic state, recent fluctuations in heart demand based upon exercise or other stress factors, and recent history of the voltages and pulsewidths used by controller 47 to pace the heart. A command from the pacemaker demand controller 43 based upon the decision in step 44 results in step 48, which is the initiation of a pulsewidth signal made up of a large number of micropulses; instructions regarding the pulse duration, spacing, and voltage level are sent to the pulsewidth controller 47 by pacemaker demand controller 43. Step 50 sends the first command to driver circuit 51. Counter 62 then increments, and instructs the pulsewidth controller 47 to repeat step 50 and send another command to driver circuit 51 that will result in another micropulse having either the same, or differing, length than the previous micropulse, depending upon the algorithm 41. This process is repeated until the micropulse train programmed into algorithm 41 has been satisfied, whereupon command 64 ends micropulse generation. Demand controller 43 may also in turn communicate with the external programmer 40, depending upon preset parameters in order to either send an alert to the patient, or to initiate information exchange with the physician who may direct some change in the course of therapy based on said information. It should be noted again that while the statements made in describing the process depicted in FIG. 7 may imply fixed values of timing and voltage for the micropulses used to pace the heart, the duration of micropulses may range from below 1 microsecond to over 100 microseconds and may be variable over time, both in absolute duration and in their ratio. Further, the supply voltage may be variable over time within a single pacing signal 10, or between pacing signals, as a function of changes in physiologic demand or based on changes in programmed response of the pacemaker system.

Referring once again to FIG. 7, upon command from the pulsewidth controller 47, driver circuit 51 creates an appropriate micropulse for delivery 52 to the heart. As will be apparent to those skilled in the art, one may use conventional pulsed signal generators as driver 51. Reference may be had, for example, to U.S. Pat. No. 4,012,641 (portable pulsed signal generator), U.S. Pat. No. 5,217,009 (compact biomedical pulsed signal generator), U.S. Pat. No. 6,011,994 (biomedical pulsed signal generator), and the like. The entire disclosure of these United States patent is hereby incorporated by reference into this specification. As will be apparent, the pulsed signal generator circuitry can produce variable outputs.

By way of further illustration, and referring to pages 14–29 et seq. of Donald G. Fink's "Electronics Engineers' Handbook," Second Edition (McGraw Hill Book Company, New York, N.Y., 1982), it will be seen that a high frequency signal made up of individual pulses, all of the same voltage, but having duty cycles less than 1.0, will produce an effective applied voltage equivalent to the duty cycle multiplied by the applied pulse voltage.

Referring again to FIG. 7, and for purposes of clarity in illustrating the utility of this invention, the pacemaker lead and electrodes 53 that send and receive energy from the heart 56A are described as parts 54A, 54B, 58A, and 58B. As shown in FIGS. 3, 4 and 5, and as described in the corresponding part of this specification, cardiac pacemaker lead 2 may be an electrical conductor or may comprise one or more optical fibers that carry light energy between the pacemaker device case and the electrodes. The embodiment employing optical means is intended to create pacemaker leads that are immune to the intense radio frequency and magnetic fields associated with magnetic resonance imaging (MRI). Thus in FIG. 7, parts 54A and 58A are similar to traditional electrical pacemaker leads and electrodes, and parts 54B and 58B are comparable optical pacemaker leads that are specifically designed to be used in an MRI diagnostic environment. Further description in this specification will refer simply to parts 54 and 58.

Parts 54 and 58 are shown in FIG. 7 as being separate. In some pacemaker system designs, the pacing and sensing functions may be conducted via the same lead and electrodes; however for reasons of clarity they are shown herein as separate. A signal from the heart 56A, indicating the initiation of a heartbeat, returns to the decision step 60, which in turn ends the micropulse pacing of the heart upon receipt of said signal.

The phenomena, devices, and methods described as parts of this invention, although described in the context of cardiac pacing, may easily be applied to other stimulatory processes, including but not limited to cardiac defibrillation, deep brain stimulation, vagas nerve stimulation, and the like. The supply voltage used for pulsewidth modulation signals for these nerve stimulation processes may be different from the supply voltage used in cardiac stimulation, as will the preferred pulsewidth modulation frequency and the overall signal waveform used in these neural stimulation processes.

Referring once again to FIG. 7, it may be seen that parts 54 and 58 may be used to sense and stimulate tissue that is may be cardiac tissue of a heart 56A, or may be brain tissue in a brain 56B, or may be vagas nerve or other nerve tissue as shown by nerve 56C.

In one preferred embodiment, there is provided a cardiac assist system comprising means for delivering a first pacing pulse from said system to a heart, means for ceasing the delivery of said first pacing pulse to said heart, and means for delivering a second pacing pulse from said system to said heart, wherein: (a) said first pacing pulse and said second pacing pulse are delivered to said heart within a period of less than about 10 milliseconds, and wherein each of said first pacing pulse and said second pacing pulse has a voltage of from about 2 to about 10 volts direct current, and the time between said delivery of said first pacing pulse and said second pacing pulse is at least about 1 microsecond, (b) said first pacing pulse and said second pacing pulse are delivered to said heart at a frequency of from about 2 kilohertz to about 5 megahertz, (c) said first pacing pulse and said second pacing pulse each have a duration of from about 1 microsecond to about 100 microseconds, and (d) said cardiac assist system is comprised of means for varying at least one property of a pacing pulse selected from the group consisting of said first pacing pulse, said second pacing pulse, and both said first pacing pulse and said second pacing pulse.

In this embodiment, the cardiac assist system is comprised of means for varying at least one of the properties of the first pacing pulse, the second pacing pulse, and/or one or more of the other pacing pulses. The properties so varied may include, e.g., the voltage, the duration, frequency, the number, the shape, etc. of the pacing pulses.

This cardiac assist system may optionally comprise means for isolating sensing electrodes from polarization potential generated by cardiac tissue as a result of pacing signals.

In another aspect of this cardiac assist system, the pulsewidth-modulated cardiac pacing signal employs individual micropulses having variable duration between about 1 microsecond and 100 microseconds.

In yet another aspect of this cardiac assist system, the system communicates with an external device to report status, to report alerts, and to accept instructions for modifications to its control algorithm.

In another preferred embodiment, there is provided an electrical stimulating system for use in deep brain stimulation, vagas nerve stimulation, or other stimulatory therapy comprising means for delivering a first pulse from said system to a nerve, means for ceasing the delivery of said first pulse, and means for delivering a second pacing pulse from said system, wherein: (a) said first pulse and said second pulse are delivered within a period of less than about 10 milliseconds, and wherein each of said first pulse and said second pulse has a voltage of from about 2 to about 20 volts direct current, and the time between said delivery of said first pulse and said second pulse is at least about 1 microsecond, (b) said first pulse and said second pacing are delivered at a frequency of from about 2 kilohertz to about 5 megahertz, (c) said first pulse and said second pulse each have a duration of from about 0.1 microseconds to about 500 milliseconds, and (d) said system is comprised of means for varying at least one property of a pulse selected from the group consisting of said first pulse, said second pulse, and both said first pulse and said second pulse.

It is to be understood that the aforementioned description is illustrative only and that changes can be made in the apparatus, in the sequence and combinations of process steps, as well as in other aspects of the invention discussed herein, without departing from the scope of the invention as defined in the following claims.

I claim:

1. A process for stimulating tissue selected from the group consisting of cardiac tissue, nerve tissue, brain tissue, and combinations thereof, comprising:
   delivering an electrical stimulating signal to the tissue, the electrical stimulating signal having about 10 to about 1,000 individual pulses, the individual pulses forming a first set of pulses and a second set of pulses, each individual pulse having a duration of from about one microsecond to about 100 microseconds, the individual pulses being discontinuous, with a spacing between adjacent pulses of at least from about 1 microsecond to about 100 microseconds, and the individual pulses each having a voltage of from about 10 millivolts to about 100 volts, the first set of pulses having a first voltage of about 10 millivolts to about 100 volts, the second set of pulses having a second voltage of about 10 millivolts to about 100 volts, the first voltage being different from the second voltage.

2. The process recited in claim 1, wherein the tissue is heart tissue and the electrical stimulating signal is delivered by a cardiac assist device.

3. The process as claim 1, wherein the tissue is brain tissue and the electrical stimulating signal is delivered by a deep brain stimulator.

4. The process as recited in claim 1, wherein the tissue is vagas nerve tissue.

5. The process as recited in claim 1, wherein the electrical stimulating signal is provided a by a stimulating device comprising a first sensing electrode and a second sensing electrode.

6. The process as recited in claim 1, wherein the electrical stimulating signal is provided a by a stimulating device comprising a first stimulating electrode and second stimulating electrode.

7. The process as recited in claim 1, wherein the individual pulses are delivered to the organ or nerve within a period of less than about 10 milliseconds, each of the pulses having a voltage of from about 2 to about 20 volts direct current, the time between the delivery of a first pulse and a second and further pulses is at least about 1 microsecond, individual pulses being delivered to the organ or nerve at a frequency of from about 2 kilohertz to about 5 megahertz, and individual pulses each having a duration of from about 0.1 microseconds to about 500 milliseconds.

8. The process as recited in claim 7, wherein the spacing between the individual pulses is from about 1 microsecond to about 100 microseconds.

9. The process as recited in claim 1, wherein the electrical signal is delivered by a device implanted within a biological organism.

10. A process for stimulating tissue selected from the group consisting of cardiac tissue, nerve tissue, brain tissue, and combinations thereof, comprising:
    delivering an electrical stimulating signal to the tissue, the electrical stimulating signal having about 10 to about 1,000 individual pulses, the individual pulses forming a first set of pulses and a second set of pulses, each individual pulse having a duration of from about one microsecond to about 100 microseconds, the individual pulses being discontinuous, with a spacing between adjacent pulses of at least from about 1 microsecond to about 100 microseconds, and the individual pulses each having a voltage of from about 10 millivolts to about 100 volts, the first set of pulses having a first duration of about one microsecond to about 100 microseconds, the second set of pulses having a second duration of about one microsecond to about 100 microseconds, the first duration being different from the second duration.

11. The process recited in claim 10, wherein the tissue is heart tissue and the electrical stimulating signal is delivered by a cardiac assist device.

12. The process as claim 10, wherein the tissue is brain tissue and the electrical stimulating signal is delivered by a deep brain stimulator.

13. The process as recited in claim 10, wherein the tissue is vagas nerve tissue.

14. The process as recited in claim 10, wherein the electrical stimulating signal is provided a by a stimulating device comprising a first sensing electrode and a second sensing electrode.

15. The process as recited in claim 10, wherein the electrical stimulating signal is provided a by a stimulating device comprising a first stimulating electrode and second stimulating electrode.

16. The process as recited in claim 1, wherein the individual pulses are delivered to the organ or nerve within a period of less than about 10 milliseconds, each of the pulses having a voltage of from about 2 to about 20 volts direct current, the time between the delivery of a first pulse and a second and further pulses is at least about 1 microsecond, individual pulses being delivered to the organ or nerve at a frequency of from about 2 kilohertz to about 5 megahertz, and individual pulses each having a duration of from about 0.1 microseconds to about 500 milliseconds.

17. The process as recited in claim 7, wherein the spacing between the individual pulses is from about 1 microsecond to about 100 microseconds.

18. The process as recited in claim 1, wherein the electrical signal is delivered by a device implanted within a biological organism.

* * * * *